May 13, 1958 O. R. BRISTOW Plant Pat. 1,706
AZALEA PLANT
Filed May 9, 1957
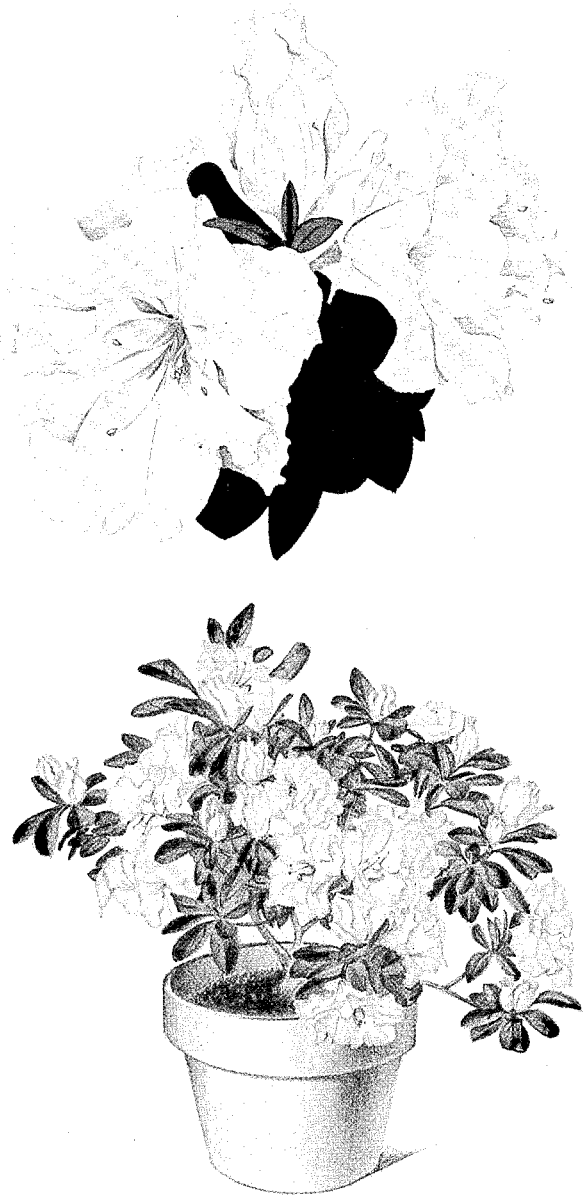
OWEN R. BRISTOW
INVENTOR.
BY Orville R. Beidner
AGENT United States Patent Office Plant Pat. 1,706
Patented May 13, 1958

1,706

AZALEA PLANT

Owen R. Bristow, San Bernardino, Calif., assignor to Mossholder Nursery, Orange County, Calif.

Application May 9, 1957, Serial No. 658,211

1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 2A for identification purposes.

The azalea of this distinct and new variety has distinguishing characteristics over known varieties which adapt it equally well to outdoor and greenhouse growth. The plant roots easily from cuttings and is a strong grower. A particularly distinctive feature is that it is an excellent forcing variety for the florist, thus providing the grower or florist with a plant having valuable commercial qualities.

In connection with its forcing quality, it should be noted that this azalea can be grown in one-third less time than the Belgian Indica varieties.

Another distinctive characteristic is that the mature foliage is a glossy deep green of the Belgian Indica type, providing an unusually attractive background for the delicately shaded flowers which are an outstanding pastel lavender color with white 'blotchings."

Yet another distinctive feature is the exceptional flower holding ability of the plant, whether of the forced variety or of an outside blooming plant.

Asexual reproduction of this distinct and new variety of azalea was accomplished by me at my nursery in San Bernardino, California, by the known method of removing cuttings from the original hybrid plant which matured from a seedling, and potting them separately from the donor plant. Subsequent reproductions of the plant in the same manner indicate that the foregoing characteristics, as well as further distinguishing characteristics brought forth in the description below, are permanently fixed, and the accompanying illustration of a forced cutting grown plant in bloom shows the prolific blooming and striking color of the flowers.

The following is a detailed specification of the plant and flower, reference being had to the authority of the Plochere Color System for color identification. The aforesaid color system has been originated by Gladys and Gustave Plochere of Los Angeles, California, to fill in certain deficiencies of color identification presently inherent in other authorities on color.

*Plant*

Form of plant: Bushy; usually somewhat broader than its height.

Growth habit: A fast grower, requiring more pinching or pruning to make bushy plants than most known varieties.

Rooting: Roots well with vigorous roots; grows strongly on its own roots.

Blooming habit: Prolific; lasting quality of flower is unusually long.

Blooming season: Late March through April in southern

California; season can be varied by early or late trimming or pinchings; easily forced for Valentine Day or Easter; an exceptional forcing variety, blooming evenly with flowers that hold exceptionally long.

*Foliage*

Size: Mature leaves average from 1½" to 2" in length and ⅝" to ⅞" wide.

Quantity: Average.

Color: New foliage, upper side light green and glossy, under side somewhat duller light green. Old foliage, upper side dark green and glossy, under side light green and flat.

Shape: Oval; slightly pointed.

Texture: Normal on both upper and under sides.

Edge or margin: Normal.

Ribs and veins: Normal.

Aspect: Glossy and slightly darker green than average known varieties.

*Flower*

Size: Average 3" to 3½" across flower.

Flowers borne: 1 to 2 on each stem; a few bear 3 on a stem.

Form: Hose-in-hose to hose-in-hose semi-double.

Quantity of bloom: Medium to abundant.

Continuity: Lasting quality is exceptionally long, making this an excellent forcing variety; some open flowers have been noted to hold for over 3 weeks on forced plants and still have fresh appearance.

Petalage:

*Size.*—1⅞" to 2⅛" long.

*Number of petals under normal conditions.*—8 to 9 on inside of hose or cycle of petals; 5 to 6 on outside hose or cycle of petals.

*Color of bud.*—First showing, Plate #388; just before opening, Plate #390.

*Color of open flower.*—Plate #391 predominantly, with shades of Plates #392 and #439 and white; dark veins in flower, Plates #389 and #390.

*Texture.*—Smooth.

Appearance: Light pastel lavender; flowers have a dark vein in petals starting at the ovary and extending out toward the edge of the petal; vein is more prominent in some of the flowers than in others; some of the petals have a creamy white blotch toward the petal tip; most flowers have a creamy white section between the throat and edge of the flower; hose-in-hose flower is characterized by ruffling on the edge of the petals which in some flowers will curl the petal in enough to give the flower the appearance of a semi-double; a few flowers in this variety have developed with several petaloids in center, making them semi-double; all flowers have a small row of petals behind the main flower, being the sepal partially developed into petals and having the same color as the rest of the flower; pistil and stamens of darker color than flowers, although most of the flowers have no stamens but a well developed pistil; a few of the flowers have 1 to 5 stamens and the pistil.

Arrangement: 1 to 3 on each stem; usually 2.

Persistence: Sets buds regularly every year.

*Reproductive organs*

Stamens: Usually none; sometimes 1 to 5.

*Anther.*—Normal: Plate #387.

*Filament.*—Normal; Plate #390 (darker than the flower).

Pollen: Little or no color.

Styles: Plate #390. Stigma—normal; pale yellow.

Ovary: Normal.

Having illustrated and described the invention, what is claimed as new and patentable is:

A distinct and new variety of azalea plant, substantially as illustrated and described hereinabove, and characterized generally by its strength of rooting and growth on its own roots, its rapid growth as a forcing variety, its glossy deep green mature foliage, and its delicate outstanding pastel lavender colored flowers with white blotchings, and particularly characterized by the exceptional holding ability of the flowers after they come into bloom.

No references cited.